US011717592B2

(12) United States Patent
Waite et al.

(10) Patent No.: US 11,717,592 B2
(45) Date of Patent: Aug. 8, 2023

(54) BIORESORBABLE DRESSING WITH STRUCTURAL SUPPORT

(71) Applicants: KCI USA, INC., San Antonio, TX (US); SYSTAGENIX WOUND MANAGEMENT, LIMITED, West Sussex (GB)

(72) Inventors: Alexander Waite, Cowling (GB); Katie Bourdillon, Leeds (GB); Craig Delury, Gargrave (GB); Daniel Parker, West Sussex (GB)

(73) Assignee: KCI Licensing, Inc., San Antonio, TX (US)

(*) Notice: Subject to any disclaimer, the term of this patent is extended or adjusted under 35 U.S.C. 154(b) by 630 days.

(21) Appl. No.: 16/625,514

(22) PCT Filed: Jul. 30, 2018

(86) PCT No.: PCT/US2018/044442
§ 371 (c)(1),
(2) Date: Dec. 20, 2019

(87) PCT Pub. No.: WO2019/027933
PCT Pub. Date: Feb. 7, 2019

(65) Prior Publication Data
US 2021/0402049 A1 Dec. 30, 2021

Related U.S. Application Data

(60) Provisional application No. 62/539,418, filed on Jul. 31, 2017.

(51) Int. Cl.
A61F 13/00 (2006.01)
A61L 15/64 (2006.01)
(Continued)

(52) U.S. Cl.
CPC ........ A61L 15/64 (2013.01); A61F 13/00012 (2013.01); A61F 13/00029 (2013.01);
(Continued)

(58) Field of Classification Search
None
See application file for complete search history.

(56) References Cited

U.S. PATENT DOCUMENTS 1,355,846 A 10/1920 Rannells
1,701,207 A * 2/1929 Johnson ............ A61F 13/00008
602/44
(Continued)

FOREIGN PATENT DOCUMENTS

AU 550575 B2 3/1986
AU 745271 B2 3/2002
(Continued)

OTHER PUBLICATIONS

EP298404 translation (Year: 2014).*
(Continued)

Primary Examiner — Kim M Lewis

(57) ABSTRACT

A dressing (as well as uses, systems, and methods including such dressing) is provided that includes a contact layer with a first surface configured to contact a tissue site in a subject and includes a scaffold configured to structurally support the contact layer, where the contact layer includes a bioresorbable material. The dressing may advantageously exhibit protease-modulating activity under physiological conditions.

14 Claims, 9 Drawing Sheets

(51) Int. Cl.
    *A61L 15/28*             (2006.01)
    *A61L 15/32*             (2006.01)
    *A61L 15/42*             (2006.01)

(52) U.S. Cl.
    CPC .. *A61F 13/00063* (2013.01); *A61F 13/00068* (2013.01); *A61L 15/28* (2013.01); *A61L 15/325* (2013.01); *A61L 15/425* (2013.01)

(56) References Cited

U.S. PATENT DOCUMENTS

| | | |
|---|---|---|
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,096,864 A * | 8/2000 | Broadley ............ C07K 5/1008 |
| | | 530/328 |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,041,868 B2 | 5/2006 | Greene et al. |
| 9,796,769 B2 * | 10/2017 | Hussain ................ A61L 15/325 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2006/0149182 A1 * | 7/2006 | Cullen ................ A61L 26/0066 |
| | | 602/41 |
| 2007/0225663 A1 * | 9/2007 | Watt ...................... A61M 1/90 |
| | | 602/42 |
| 2009/0192429 A1 * | 7/2009 | Daniels ............ A61F 13/00008 |
| | | 602/43 |
| 2011/0015586 A1 | 1/2011 | Orgill et al. |
| 2020/0390570 A1 * | 12/2020 | Mangiardi ........... A61K 31/337 |

FOREIGN PATENT DOCUMENTS

| | | | |
|---|---|---|---|
| AU | 755496 B2 | 12/2002 | |
| CA | 2005436 A1 | 6/1990 | |
| DE | 26 40 413 A1 | 3/1978 | |
| DE | 43 06 478 A1 | 9/1994 | |
| DE | 29 504 378 U1 | 9/1995 | |
| EP | 0100148 A1 | 2/1984 | |
| EP | 0117632 A2 | 9/1984 | |
| EP | 0161865 A2 | 11/1985 | |
| EP | 303496 A * | 2/1989 | ............ A61L 27/18 |
| EP | 0358302 A2 | 3/1990 | |
| EP | 431479 A1 | 6/1991 | |
| EP | 1018967 A1 | 7/2000 | |
| EP | 1795210 B1 | 6/2007 | |
| EP | 2984047 A1 * | 2/2016 | ............ A61L 15/08 |
| GB | 692578 A | 6/1953 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2314842 A | 1/1998 | |
| GB | 2 329 127 A | 3/1999 | |
| GB | 2 333 965 A | 8/1999 | |
| GB | 2370508 A * | 7/2002 | ......... A61F 13/0203 |
| JP | 4129536 B2 | 8/2008 | |
| SG | 71559 | 4/2002 | |

(56) References Cited

FOREIGN PATENT DOCUMENTS

| WO | 80/02182 A1 | 10/1980 | |
|---|---|---|---|
| WO | 87/04626 A1 | 8/1987 | |
| WO | 90/010424 A1 | 9/1990 | |
| WO | 93/009727 A1 | 5/1993 | |
| WO | 93/10731 A1 | 6/1993 | |
| WO | 94/020041 A1 | 9/1994 | |
| WO | 96/05873 A1 | 2/1996 | |
| WO | 97/18007 A1 | 5/1997 | |
| WO | 99/13793 A1 | 3/1999 | |
| WO | WO-2005105175 A1 * | 11/2005 | .......... A61M 1/0058 |
| WO | WO-2005/123170 A1 | 12/2005 | |
| WO | 2018/035063 A1 | 2/2018 | |

OTHER PUBLICATIONS

Www.thesaurus.com/browse/embedded.*

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, Md., et al.; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture" Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax, "Journal of the American Medical Association 64 (1915), pp. 1548-1549.

Selections from W. Meyer and V. Schmieden, Bier's Hyperemic Treatment in Surgery, Medicine, and the Specialties: A Manual of its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

(56) References Cited

OTHER PUBLICATIONS

International Search Report and Written Opinion in International Application No. PCT/US2018/044442, dated Oct. 16, 2018.

\* cited by examiner

BIORESORBABLE DRESSING WITH STRUCTURAL SUPPORT

CROSS-REFERENCE TO RELATED APPLICATIONS

The present application is a US national phase application under 35 USC § 371 of International Application No. PCT/US2018/044442, filed on Jul. 30, 2018, which claims the benefit of and priority to U.S. Provisional Patent Application No. 62/539,418, filed Jul. 31, 2017, the entire contents of each of which are incorporated herein by reference.

TECHNICAL FIELD

This application provides technology generally related to treatment of a tissue site and, more particularly, but without limitation, to dressings for application to a tissue site, to systems including such dressings, and to methods related to the same.

BACKGROUND

A wide variety of materials and devices, generally characterized as "dressings," are generally known in the art for use in treating an injury or other disruption of tissue. Such wounds may be the result of trauma, surgery, or disease, and may affect skin or other tissues. In general, dressings may control bleeding, absorb wound exudate, ease pain, assist in debriding the wound, protect wound tissue from infection, or otherwise promote healing and protect the wound from further damage.

Some dressings may protect tissue from, or even assist in the treatment of, infections associated with wounds. Infections can delay wound healing and, if untreated, can result in tissue loss, systemic infections, septic shock and death. While the benefits of dressings are widely accepted, improvements to dressings may benefit healthcare providers and patients.

SUMMARY

Dressings and methods for using a dressing, for example, in a therapy environment, are set forth in the appended claims. Illustrative embodiments are also provided to enable a person skilled in the art to make and use the claimed subject matter.

For example, some embodiments of a dressing may comprise a contact layer and a scaffold configured to structurally support the contact layer. The contact layer may exhibit protease-modulating activity and may comprise a bioresorbable material, for example, collagen and oxidized regenerated cellulose.

Also, some embodiments a method for providing therapy to a tissue site may comprise positioning a dressing adjacent to the tissue site. The dressing may comprise a contact layer and a scaffold configured to structurally support the contact layer. The contact layer may exhibit protease-modulating activity and may comprise a bioresorbable material, for example, collagen and oxidized regenerated cellulose.

Objectives, advantages, and a preferred mode of making and using the claimed subject matter may be understood best by reference to the accompanying drawings in conjunction with the following detailed description of illustrative embodiments.

Figure 1:
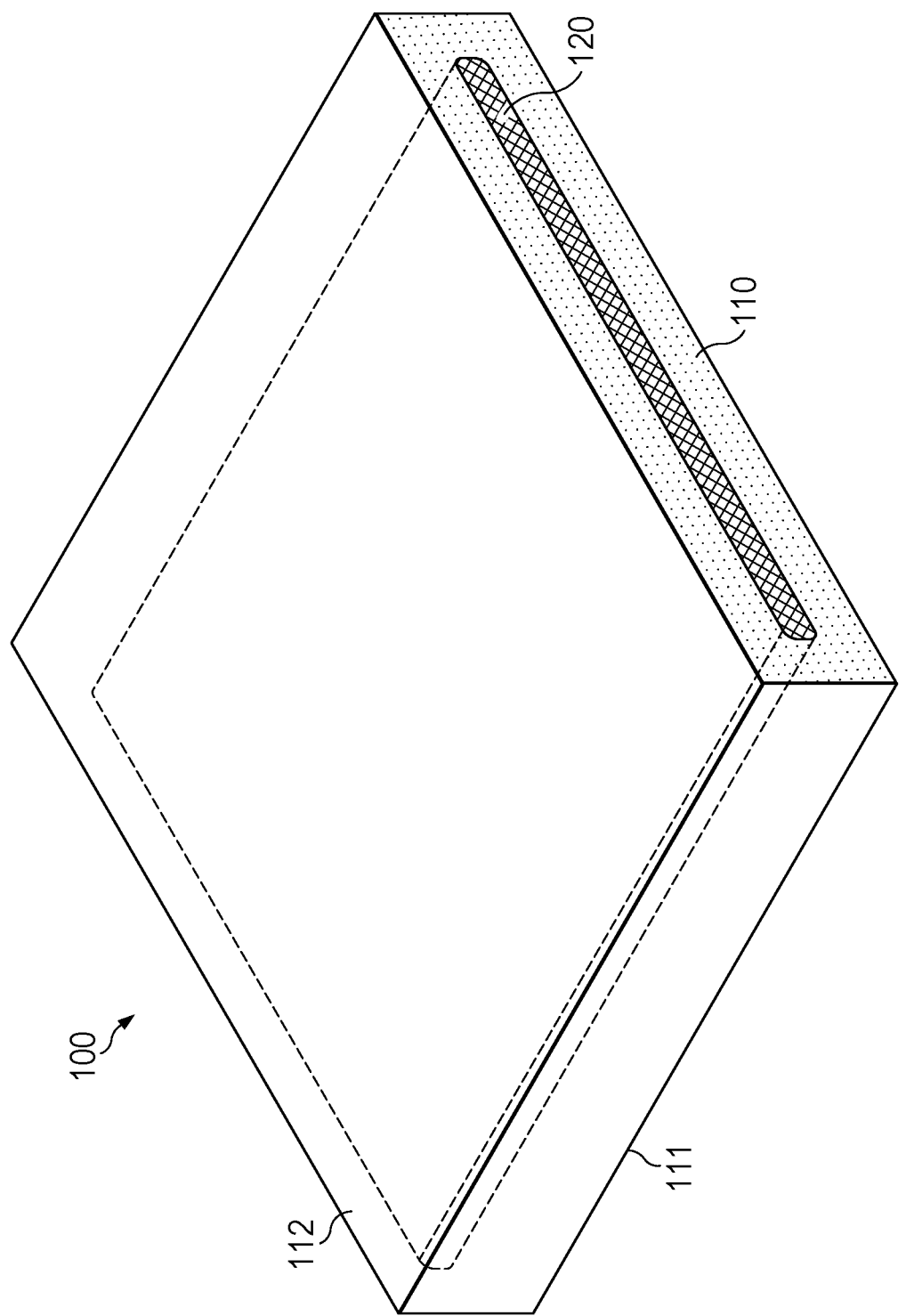
FIG. 1 is an illustrative representation of a cross-sectional, perspective view of an embodiment of a dressing of the present technology.

It should be noted that the representative illustrations provided in the figures set forth herein are intended to illustrate the general features and/or characteristics of certain exemplary embodiments to aid in describing the present technology in full. The figures may not precisely reflect the characteristics of any given embodiment, and are not necessarily intended to define or limit the scope of the claimed subject matter. Further, the present technology may or may not include or incorporate therewith any one or more features or characteristics set provided in any one or more figures.

DESCRIPTION

The present technology provides dressings, various layers thereof, and therapy systems including such dressings and/or layers, as well as methods including any embodiment disclosed herein of such dressings, various layers thereof, and/or therapy systems. Generally, and as will be disclosed herein, the dressings of the present technology may be configured to provide therapy to a tissue site. The following description provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

"Tissue site" as used herein refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, grafts, or a combination of any two or more thereof. The term "tissue site" also refers to areas of any tissue that are not necessarily wounded or defective, but are instead areas in which it may be desirable to add or promote the growth of additional tissue.

As used herein, the term "effective amount" refers to a quantity sufficient to achieve a desired therapeutic effect, e.g., an amount which results in the decrease in a wound described herein or one or more signs or symptoms associated with a wound described herein. In the context of therapeutic applications, the amount of a composition administered to the subject will vary depending on the composition, the degree, type, and severity of the wound and on the characteristics of the individual. The compositions can also be administered in combination with one or more additional therapeutic compounds. In the methods described herein, the therapeutic compositions may be administered to a subject having one or more wounds.

As used herein, the terms "individual", "patient", or "subject" can be an individual organism, a vertebrate, a mammal, or a human. In some embodiments, the individual, patient or subject is a human.

"Treating" or "treatment" as used herein includes: (i) inhibiting a wound of a subject, i.e., arresting its development; (ii) relieving a wound of a subject, i.e., causing regression of the wound; (iii) slowing progression of a wound of a subject; and/or (iv) inhibiting, relieving, and/or slowing progression of one or more symptoms of a wound of a subject. Such treatment means that the symptoms associated with the wound are, e.g., alleviated, reduced, cured, or placed in a state of remission.

It is also to be appreciated that the various modes of treatment of wounds as described herein are intended to include total as well as less than total treatment wherein some biologically or medically relevant result is achieved. The treatment may be a continuous prolonged treatment for e.g., a chronic wound, or a single, or few time administrations for treatment of e.g., an acute wound.

Dressings of the Present Technology

In an aspect, the present technology provides a dressing that includes a contact layer and a scaffold configured to structurally support the contact layer. The contact layer includes a bioresorbable material as well as a first surface configured to contact a tissue site in a subject. FIG. 1 provides an illustrative illustration of a dressing 100 that includes a contact layer 110 and a scaffold 120. While not illustrated in FIG. 1, the dressing may include one or more layers in addition to the contact layer (described further herein). In any embodiment herein, the contact layer, the scaffold, or both may be configured to contact a portion of the tissue site, substantially all of the tissue site, or the tissue site in its entirety. If the tissue site is a wound, for example, the dressing or a portion of the dressing may partially or completely fill the wound, and/or may be placed over the wound. Dressing of the present technology may take many forms, and may have many sizes, shapes, and/or thicknesses depending on a variety of factors, such as the type of treatment being implemented or the nature and/or size of a tissue site. For example, the size and shape of the contact layer, the scaffold, or both may be adapted to the contours of deep and irregular shaped tissue sites and/or may be configured so as to be adaptable to a given shape or contour. Further, in any embodiment herein, any one or more surfaces of the dressing may include projections and/or an uneven, course, or jagged profile configured to induce strains and stresses on the tissue site effective to promote granulation at the tissue site.

Contact Layer

In any embodiment herein, the contact layer may be generally configured to exhibit biological activity, such as protease-modulating activity, under physiological conditions, such as when the first surface is contacted with the tissue site. The bioresorbable material of the contact layer may be configured in the form a film, a foam, a fibrous substrate, and/or other physical structure of the contact layer.

In any embodiment herein, the bioresorbable material may include an oxidized cellulose, such as an oxidized regenerated cellulose (ORC). Oxidized cellulose may be produced by the oxidation of cellulose, for example with dinitrogen tetroxide. Not wishing to be bound by theory, it is believed that, the oxidation of cellulose converts primary alcohol groups on the saccharide residues to carboxylic acid group, forming uronic acid residues within the cellulose chain. The oxidation may not proceed with complete selectivity, and as a result hydroxyl groups on carbons 2 and 3 may be converted to the keto form. These ketone units yield an alkali labile link, which at a pH of about 7 or higher may initiate the decomposition of the polymer via formation of a lactone and sugar ring cleavage. As a result, oxidized cellulose is biodegradable and bioabsorbable under physiological conditions.

In any embodiment herein, the oxidized cellulose may be ORC prepared by oxidation of a regenerated cellulose, such as rayon. ORC may be manufactured, for example, by the process described in U.S. Pat. No. 3,122,479, issued Feb. 24, 1964, which is incorporated herein by reference in its entirety. ORC is available with varying degrees of oxidation and hence rates of degradation. Additionally or alternatively, in some embodiments, the ORC may be in the form of water-soluble low molecular weight fragments obtained by alkali hydrolysis of ORC.

In any embodiment herein, the ORC may be included in one or more physical forms, such as particles, fibers, sheets, sponges, or fabrics (such as woven fabrics, non-woven fabrics, and/or knitted fabrics). In any embodiment herein, the bioresorbable material may include ORC in the form of particles, such as fiber particles or powder particles, for example dispersed in the contact layer. The bioresorbable material of any embodiment herein may include ORC fibers where a volume fraction of at least 80% of the ORC fibers have lengths in the range from about 5 μm to about 50 mm. In any embodiment herein, a volume fraction of at least 80% of the ORC fibers may have lengths in the range from about 5 μm to about 1000 μm, such as from about 250 μm to about 450 μm; thus, the volume fraction of at least 80% of the ORC fibers included in any embodiment herein may have lengths of about 5 μm, about 6 μm, about 7 μm, about 8 μm, about 9 μm, about 10 μm, about 11 μm, about 12 μm, about 13 μm, about 14 μm, about 15 μm, about 16 μm, about 17 μm, about 18 μm, about 19 μm, about 20 μm, about 22 μm, about 24 μm, about 26 μm, about 28 μm, about 30 μm, about 32 μm, about 34 μm, about 36 μm, about 38 μm, about 40 μm, about 42 μm, about 44 μm, about 46 μm, about 48 μm, about 50 μm, about 55 μm, about 60 μm, about 65 μm, about 70 μm, about 75 μm, about 80 μm, about 85 μm, about 90 μm, about 95 μm, about 100 μm, about 110 μm, about 120 μm, about 130 μm, about 140 μm, about 150 μm, about 160 μm, about 170 μm, about 180 μm, about 190 μm, about 200 μm, about 220 μm, about 230 μm, about 240 μm, about 250 μm, about 260 μm, about 280 μm, about 300 μm, about 320 μm, about 340 μm, about 360 μm, about 380 μm, about 400 μm, about 420 μm, about 440 μm, about 460 μm, about 480 μm, about 500 μm, about 550 μm, about 600 μm, about 650 μm, about 700 μm, about 750 μm, about 800 μm, about 850 μm, about 900 μm, about 950 μm, about 1000 μm, or any range including and/or in between any two of the preceding values. Alternatively in any embodiment herein, the volume fraction of at least 80% of ORC the fibers have lengths in the range from about 25 mm to about 50 mm; thus, the volume fraction of at least 80% of the ORC fibers have lengths of about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, about 49 mm, about 50 mm, or any range including and/or in between any two of the preceding values. Desired volume fraction distributions may be achieved, for example, by milling an ORC cloth followed by sieving the milled powder to remove fibers outside the desired range.

In any embodiment herein, the bioresorbable material may include ORC in an of about 10% to about 80% by weight of the contact layer (e.g., from about 30% to about 60% by weight of the contact layer; from about 40% to about 50% by weight of the contact layer. Thus, in any embodiment herein, the bioresorbable material may include ORC in an amount by weight of the contact layer of about 10%, about 11%, about 12%, about 13%, about 14%, about 15%, about 16%, about 17%, about 18%, about 19%, about 20%, about 22%, about 24%, about 26%, about 28%, about 30%, about 32%, about 34%, about 36%, about 38%, about 40%, about 42%, about 44%, about 46%, about 48%, about 50%, about 52%, about 54%, about 56%, about 58%, about 60%, about 62%, about 64%, about 66%, about 68%, about 70%, about 72%, about 74%, about 76%, about 78%, about 80%, or any range including and/or in between any two of the preceding values.

In any embodiment herein, the bioresorbable material may include a structural protein. Examples of suitable structural proteins include, but are not limited to, fibronectin, fibrin, laminin, elastin, collagen, gelatins, and mixtures thereof. Thus, in any embodiment herein, the bioresorbable material may include collagen. The collagen may be obtained from any natural source. The collagen may be Type I, II or III collagen, or may also be chemically modified collagen, for example, an atelocollagen obtained by removing the immunogenic telopeptides from natural collagen. The collagen may also include solubilized collagen or soluble collagen fragments. The collagen may have a weight-average molecular weight from about 5,000 to about 100,000. Thus, in any embodiment herein, the bioresorbable material may include collagen with a weight-average molecular weight of about 5,000, about 6,000, about 7,000, about 8,000, about 9,000, about 10,000, about 11,000, about 12,000, about 13,000, about 14,000, about 15,000, about 16,000, about 17,000, about 18,000, about 19,000, about 20,000, about 22,000, about 24,000, about 26,000, about 28,000, about 30,000, about 32,000, about 34,000, about 36,000, about 38,000, about 40,000, about 42,000, about 44,000, about 46,000, about 48,000, about 50,000, about 52,000, about 54,000, about 56,000, about 58,000, about 60,000, about 62,000, about 64,000, about 66,000, about 68,000, about 70,000, about 72,000, about 74,000, about 76,000, about 78,000, about 80,000, about 82,000, about 84,000, about 86,000, about 88,000, about 90,000, about 92,000, about 94,000, about 96,000, about 98,000, about 100,000, or any range including and/or in between any two of the preceding values. In any embodiment herein, the collagen may be obtained from bovine corium that has been rendered largely free of non-collagenous components. Exemplary non-collagenous components include fat, non-collagenous proteins, polysaccharides, and other carbohydrates, as described in U.S. Pat. No. 4,614,794, issued Sep. 30, 1986 and U.S. Pat. No. 4,320,201, issued Mar. 16, 1982, each of which is incorporated by reference herein.

In any embodiment herein, the bioresorbable material may include a structural protein in an amount of about 20% to about 90% by weight of the contact layer (e.g., from about 40% to about 70% by weight of the contact layer; about 50% to about 60% by weight of the contact layer). In any embodiment herein, the bioresorbable material may include collagen in an amount of about 20% to about 90% by weight of the contact layer; thus, the bioresorbable material may include collagen in an amount by weight of the contact layer of about 20%, about 22%, about 24%, about 26%, about 28%, about 30%, about 32%, about 34%, about 36%, about 38%, about 40%, about 42%, about 44%, about 46%, about 48%, about 50%, about 52%, about 54%, about 56%, about 58%, about 60%, about 62%, about 64%, about 66%, about 68%, about 70%, about 72%, about 74%, about 76%, about 78%, about 80%, about 82%, about 84%, about 86%, about 88%, about 90%, or any range including and/or in between any two of the preceding values.

In any embodiment disclosed herein, the bioresorbable material may include both ORC and collagen. For example, the bioresorbable material may include ORC from about 40% to about 50% by weight of the contact layer (e.g., about 45% by weight of the contact layer), and may include collagen from about 50% to about 60% by weight of the contact layer (e.g., about 55% by weight of the contact layer. Thus, the bioresorbable material may include ORC in an amount by weight of the contact layer of about 40%, about 41%, about 42%, about 43% t, about 44%, about 45%, about 46%, about 47%, about 48%, about 49%, about 50%, or any range including and/or in between any two of the preceding values, and may include collagen in an amount by weight of the contact layer of about 50%, about 51%, about 52%, about 53%, about 54%, about 55%, about 56%, about 57%, about 58%, about 59%, about 60%, or any range including and/or in between any two of the preceding values.

In any embodiment herein, the bioresorbable material may further include one or more of a preservative, a stabilizing agent, a hydrogel, a gelling agent, a plasticizer, a matrix strengthening material, a dyestuff, or an active ingredient where each, when present, may be present in a safe and effective amount. As referred to herein, a "safe and effective" amount of a material used herein, refers to an amount that is sufficient to impart a desired effect without undue adverse side effects (such as toxicity, irritation, or allergic response), commensurate with a reasonable benefit/risk ratio when used in the manner of this technology. The specific safe and effective amount of a particular material may vary with such factors as the type and quantity of other materials in the composition, the intended use, and the physical condition of the subject to whom the biologically-active compositions are given, and the form in which the biologically-active compositions are employed.

Gelling agents for inclusion in the bioresorbable material include, for example, a hydrophilic polysaccharide. Examples of hydrophilic polysaccharides include, but are not limited to, an alginate, chitosan, chitin, a guar gum, pectin, a starch derivative, a cellulose derivative (such as hydroxyethyl cellulose, hydroxylpropyl cellulose, and/or hydroxypropylmethyl cellulose), a glycosaminoglycan, a galactomannan, a chondroitin salt (such as chondroitin sulfate), a heparin salt (such as heparin sulfate), hyaluronic acid, a salt of hyaluronic acid, a hyaluronate, or mixtures of any two or more thereof.

In any embodiment herein, the bioresorbable material may include carboxymethyl cellulose ("CMC") to modify the rheological, absorbency, and/or other characteristics of the bioresorbable material and/or the contact layer 110. The CMC may be derived from cellulose and modified such that carboxymethyl groups are bonded to hydroxyl groups in the glucopyranose monomers that make up the cellulose. In any embodiment herein, the CMC may be in a salt form (e.g., sodium carboxymethyl cellulose). CMC is commercially available as Walocel™ (sold by The Dow Chemical Company) and Cekol® (sold by CP Kelco). When present in the bioresorbable material, the CMC may be present at any amount appropriate to result in the desired characteristics for the bioresorbable material.

As discussed above, the bioresorbable material may include a strengthening material which can improve the handling characteristics of the substrate. For example, a strengthening material can decrease a substrate's susceptibility to tearing. Non-gelling cellulose fibers are an example of a strengthening material, where such "non-gelling" cellulose fibers may be substantially water-insoluble and may be produced from cellulose that has not been chemically modified to increase water solubility (as contrasted from carboxymethyl cellulose or other cellulose ethers). Non-gelling cellulose fibers are commercially available (e.g., Tencel® fibers sold by Lenzing AG). The non-gelling cellulose fibers may be processed from a commercially-available continuous length, by cutting into lengths that are about 0.5 cm to about 5 cm, in length. Thus, in any embodiment herein, the bioresorbable material may include non-gelling cellulose fibers with a length of about 0.5 cm, about 0.6 cm, about 0.7 cm, about 0.8 cm, about 0.9 cm, about 1 cm, about 1.1 cm, about 1.2 cm, about 1.3 cm, about 1.4 cm, about 1.5 cm, about 1.6 cm, about 1.7 cm, about 1.8 cm, about 1.9 cm, about 2 cm, about 2.1 cm, about 2.2 cm, about 2.3 cm, about 2.4 cm, about 2.5 cm, about 2.6 cm, about 2.7 cm, about 2.8 cm, about 2.9 cm, about 3 cm, about 3.1 cm, about 3.2 cm, about 3.3 cm, about 3.4 cm, about 3.5 cm, about 3.6 cm, about 3.7 cm, about 3.8 cm, about 3.9 cm, about 4 cm, about 4.1 cm, about 4.2 cm, about 4.3 cm, about 4.4 cm, about 4.5 cm, about 4.6 cm, about 4.7 cm, about 4.8 cm, about 4.9 cm, about 5 cm, or any range including and/or in between any two of the preceding values. The non-gelling cellulose fibers may be present in the bioresorbable material at any level appropriate to result in the desired physical characteristics of the contact layer.

As discussed previously, in any embodiment herein the bioresorbable material may include one or more active ingredients. Such active ingredients may, for example, aid in wound healing. Exemplary active ingredients include, but are not limited to, a non-steroidal anti-inflammatory drug, acetaminophen, a steroid, an antibiotic, an antiseptic (e.g., silver and/or chlorhexidine), and a growth factor (e.g., a platelet derived growth factor (PDGF), a fibroblast growth factor (FGF), an epidermal growth factor (EGF)). In any embodiment herein, the one or more active ingredients may be present at a an amount of about 0.1% to about 10% by weight of the contact layer; thus, the bioresorbable material may include one or more active ingredients in an amount by weight of the contact layer of about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.2%, about 2.4%, about 2.6%, about 2.8%, about 3%, about 3.2%, about 3.4%, about 3.6%, about 3.8%, about 4%, about 4.2%, about 4.4%, about 4.6%, about 4.8% about 5%, about 5.2%, about 5.4%, about 5.6%, about 5.8%, about 6%, about 6.2%, about 6.4%, about 6.6%, about 6.8%, about 7%, about 7.2%, about 7.4%, about 7.6%, about 7.8%, about 8%, about 8.2%, about 8.4%, about 8.6%, about 8.8%, about 9%, about 9.2%, about 9.4%, about 9.6%, about 9.8%, about 10%, or any range including and/or in between any two of the preceding values.

As discussed above, the bioresorbable material may include an antimicrobial agent, an antiseptic, or both. Examples of antimicrobial agents include, but are not limited to, a tetracycline, a penicillin, a terramycin, an erythromycin, bacitracin, neomycin, polymycin B, mupirocin, clindamycin, or a combination of any two or more thereof. Examples of antiseptics include, but are not limited to silver, polyhexanide (polyhexamethylene biguanide or PHMB), chlorhexidine, povidone iodine, triclosan, sucralfate, quaternary ammonium salts, or a combination of any two or more thereof. In any embodiment herein, the bioresorbable material may include silver, which may be in metallic form, in ionic form (e.g., a silver salt), or both. The bioresorbable material may include a complex of silver and ORC (a "Silver/ORC complex"). As referred to herein, such a complex is an intimate mixture at the molecular level, for example, with ionic or covalent bonding between the silver and the ORC. The Silver/ORC complex may include a salt formed between the ORC and $Ag^+$, but it may also include silver clusters and/or colloidal silver metal (for example, produced by exposure of the complex to light). The Silver/ORC complex may be made by treating ORC with a solution of a silver salt, where the silver salt may be the salt of silver with a weak acid. Silver/ORC complexes useful herein, and methods of producing such complexes, are described in U.S. Pat. No. 8,461,410, issued Jun. 11, 2013, incorporated by reference herein. Similar processes are described in U.S. Pat. No. 5,134,229, issued Jul. 28, 1992, each of which is incorporated by reference herein. The Silver/ORC Complex may be present from about 1% to about 2% by weight of the contact layer.

As discussed above, in any embodiment herein the bioresorbable material may include a dyestuff. The dyestuff may be light-absorbing in the visible region 400-700 nm. Without wishing to be bound by theory, such dyestuffs may be operable to photochemically trap generated free radicals that could otherwise react with the silver in the present compositions, acting as photochemical desensitizers (an "antioxidant dyestuff"). Exemplary antioxidant dyestuffs include, but are not limited to, aniline dyes, acridine dyes, thionine dyes, bis-naphthalene dyes, thiazine dyes, azo dyes, anthraquinone dyes, gentian violet, aniline blue, methylene blue, crystal-violet, acriflavine, 9-aminoacridine, acridine yellow, acridine orange, proflavin, quinacrine, brilliant green, trypan blue, trypan red, malachite green, azacrine, methyl violet, methyl orange, methyl yellow, ethyl violet, acid orange, acid yellow, acid blue, acid red, thioflavin, alphazurine, indigo blue, methylene green, or a combination of any two or more thereof. The dyestuff (e.g., an antioxidant dyestuff) may be included in the bioresorbable material in an amount of about 0.05% to about 5% by weight of the contact layer (e.g., about 0.2% to about 2% by weight of the contact layer).

In any embodiment herein, the contact layer may be biodegradable and/or exhibit biodegradability. As used herein, "biodegradable" and "biodegradability" may refer to a characteristic of a material to at least partially break down upon exposure to physiological fluids or processes. In any embodiment herein, the contact layer may disintegrate, degrade, and/or dissolve when contacted with an aqueous medium, such as water, blood, or wound exudate from a tissue site. Biodegradability may result from a chemical process, a physical process and/or condition, or a combination of any two or more thereof.

The contact layer may be configured to exhibit a particular proportion of disintegration, degradation, and/or dissolution (hereafter collectively referred to as "broken down") within a particular time period. In any embodiment herein, the contact layer 110 may be configured such that about 90% by weight, about 91% by weight, about 92% by weight, about 93% by weight, about 94% by weight, about 95% by weight, about 96% by weight, about 97% by weight, about 98% by weight, about 99% by weight, or about 100% by weight of the contact layer (or any range including and/or in between any two of these values) may be broken down within a time period of about 24 hours, about 26 hours, about 28 hours, about 30 hours, about 32 hours, about 34 hours, about 36 hours, about 38 hours, about 40 hours, about 42 hours, about 44 hours, about 46 hours, about 48 hours, about 2 days, about 3 days, about 4 days, about 5 days, about 6 days, about 7 days, or any range including and/or in between any two of these values, from introduction into a physiological environment or when incubated with simulated physiological fluid at a temperature of about 37° C. In any embodiment herein, a portion of the contact layer may be non-bioresorbable.

In any embodiment herein, the contact layer may be configured to modulate protease activity. For example, contact with wound fluid, such as wound exudate, may cause the contact layer to break down into products that may have the effect of modulating protease activity. Modulating protease activity may include inhibiting protease activity. For example, the disintegration, degradation, and/or dissolution products of collagen and/or ORC may be effective to inhibit the activity of destructive enzymes such as neutrophil elastase and matrix metalloproteinase (MMP). Thus, in any embodiment herein, the contact layer may be configured to be effective to inhibit protease activity such that protease activity is decreased to less than about 75% of the protease activity that would be present if uninhibited, or to less than about 50%, more particularly, to less than about 40%, or to less than about 30%, more particularly, to less than about 20%, or to less than about 10%, more particularly, to less than about 5%, or to less than about 1% of the protease activity than would be present if uninhibited.

In any embodiment herein, the contact layer may include water in an amount by weight of the contact layer of about 10% or less. Thus, the contact layer may include water in an amount by weight of the contact layer of about 10%, about 9%, about 8%, about 7%, about 6%, about 5%, about 4%, about 3%, about 2%, about 1%, or any range including and/or in between any two of the preceding values. In any embodiment herein, the contact layer 110 may be freeze-dried.

The contact layer may be in a form that includes a film, a sheet, a foam (such as an open-cell foam), a fibrous substrate (such as a woven and/or non-woven mesh), or a combination of any two or more thereof. As illustrated in FIG. 1, the contact layer (110) may include a generally flat structure having two opposite-facing planar surfaces and a depth or thickness orthogonal to the planar surfaces. In any embodiment herein, the contact layer (110) may include a first surface (111), which may be configured to face a tissue site, and a second surface (112), which may be configured to face away from a tissue site. The first surface may have a surface area from about 1 $cm^2$ to about 400 $cm^2$, from about 2 $cm^2$ to about 200 $cm^2$, or from about 4 $cm^2$ to about 100 $cm^2$. Thus, the first surface of the contact layer may have a surface area of about 1 $cm^2$, about 2 $cm^2$, about 3 $cm^2$, about 4 $cm^2$, about 5 $cm^2$, about 6 $cm^2$, about 7 $cm^2$, about 8 $cm^2$, about 9 $cm^2$, about 10 $cm^2$, about 11 $cm^2$, about 12 $cm^2$, about 13 $cm^2$, about 14 $cm^2$, about 15 $cm^2$, about 16 $cm^2$, about 17 $cm^2$, about 18 $cm^2$, about 19 $cm^2$, about 20 $cm^2$, about 22 $cm^2$, about 24 $cm^2$, about 26 $cm^2$, about 28 $cm^2$, about 30 $cm^2$, about 32 $cm^2$, about 34 $cm^2$, about 36 $cm^2$, about 38 $cm^2$, about 40 $cm^2$, about 42 $cm^2$, about 44 $cm^2$, about 46 $cm^2$, about 48 $cm^2$, about 50 $cm^2$, about 52 $cm^2$, about 54 $cm^2$, about 56 $cm^2$, about 58 $cm^2$, about 60 $cm^2$, about 62 cm², about 64 cm², about 66 cm², about 68 cm², about 70 cm², about 72 cm², about 74 cm², about 76 cm², about 78 cm², about 80 cm², about 82 cm², about 84 cm², about 86 cm², about 88 cm², about 90 cm², about 92 cm², about 94 cm², about 96 cm², about 98 cm², about 100 cm², about 110 cm², about 120 cm², about 130 cm², about 140 cm², about 150 cm², about 160 cm², about 170 cm², about 180 cm², about 190 cm², about 200 cm², about 210 cm², about 220 cm², about 230 cm², about 240 cm², about 250 cm², about 260 cm², about 270 cm², about 280 cm², about 290 cm², about 300 cm², about 310 cm², about 320 cm², about 330 cm², about 340 cm², about 350 cm², about 360 cm², about 370 cm², about 380 cm², about 390 cm², about 400 cm², or any range including and/or in between any two of the preceding values. While not illustrated in FIG. 1, the first surface and the second surface may (independently of each other) have any suitable shape, examples of which include but are not limited to, triangles, squares, rectangles, ellipses, circles, ovals, and various polygons having four, five, six, seven, eight, or more sides. It will be understood that the shape and area of the various surfaces may be customized to the location and type of tissue onto which the dressing may be applied. Similarly, the various physical properties and parameters associated with the contact layer, such as tensile strength, may be varied according to a prescribed therapy.

Scaffold

The scaffold of the dressing is configured to structurally support the contact layer. For example, the scaffold may be configured to retain the contact layer in a particular, desired conformation. Additionally or alternatively, the scaffold may be configured to limit the movement of the contact layer, such as to limit flexure, folding, bending, twisting, stretching, or a combination of any two or more thereof. In any embodiment herein, the scaffold may be configured to maintain the contact layer in a flat or substantially flat conformation. The scaffold may be configured to allow the contact layer to experience or undergo not more than a desired degree of flexure, bending, or stretching—for example, the scaffold may allow the contact layer to flex, bend, or stretch to such a degree as necessary to be conformed to one or more surfaces of a tissue site, such as a wound, while keeping the contact layer from folding or doubling over.

In any embodiment herein, the scaffold may include a suitable, biocompatible material. As used herein, "biocompatible" and "biocompatibility" may refer to a characteristic of a material to be suitable for use with living tissue. A biocompatible material may be characterized as substantially non-toxic, as substantially non-injurious, as not eliciting a substantial impairment of biological tissue function, as not eliciting a substantial immunological response, or combinations thereof. In any embodiment herein, it may be the biocompatible material is not a bioresorbable material. The biocompatible material of the scaffold may be configured to be non-adherent or minimally-adherent with respect to the tissue site. For example, the biocompatible material may exhibit relatively little tendency to adhere or stick to proximate tissue. Exemplary biocompatible materials of the scaffold include, but are not limited to, viscose, cotton, rayon, nylon, silk, silicon, a thermoplastic material, a cellulose, a cellulosic derivative, an alginate, as well as a combination of any two or more thereof.

In any embodiment herein, the scaffold may include a bioresorbable material. In any embodiment herein, the bioresorbable material of the scaffold may be configured to be less degradable than the bioresorbable material of the contact layer—for example, the scaffold may be configured to disintegrate, degrade, and/or dissolve more slowly than the contact layer. Examples of a suitable material for use as the bioresorbable material of the scaffold include, but are not limited to, oxidized cellulose, ORC, or a combination thereof.

The scaffold may be in a form that includes a film, a sheet, a fibrous substrate (such as a knitted or woven sheet or non-woven mesh), a plurality of strips (such as filaments, rods, and/or ribbons), or a combination of any two or more thereof. In any embodiment herein, the scaffold may include one or more pores or apertures. Such pores and/or apertures may be configured to provide a pathway of fluid communication through the scaffold. The size and distribution of the pores or apertures may be varied according to the needs a particular therapy.

Figure 2:
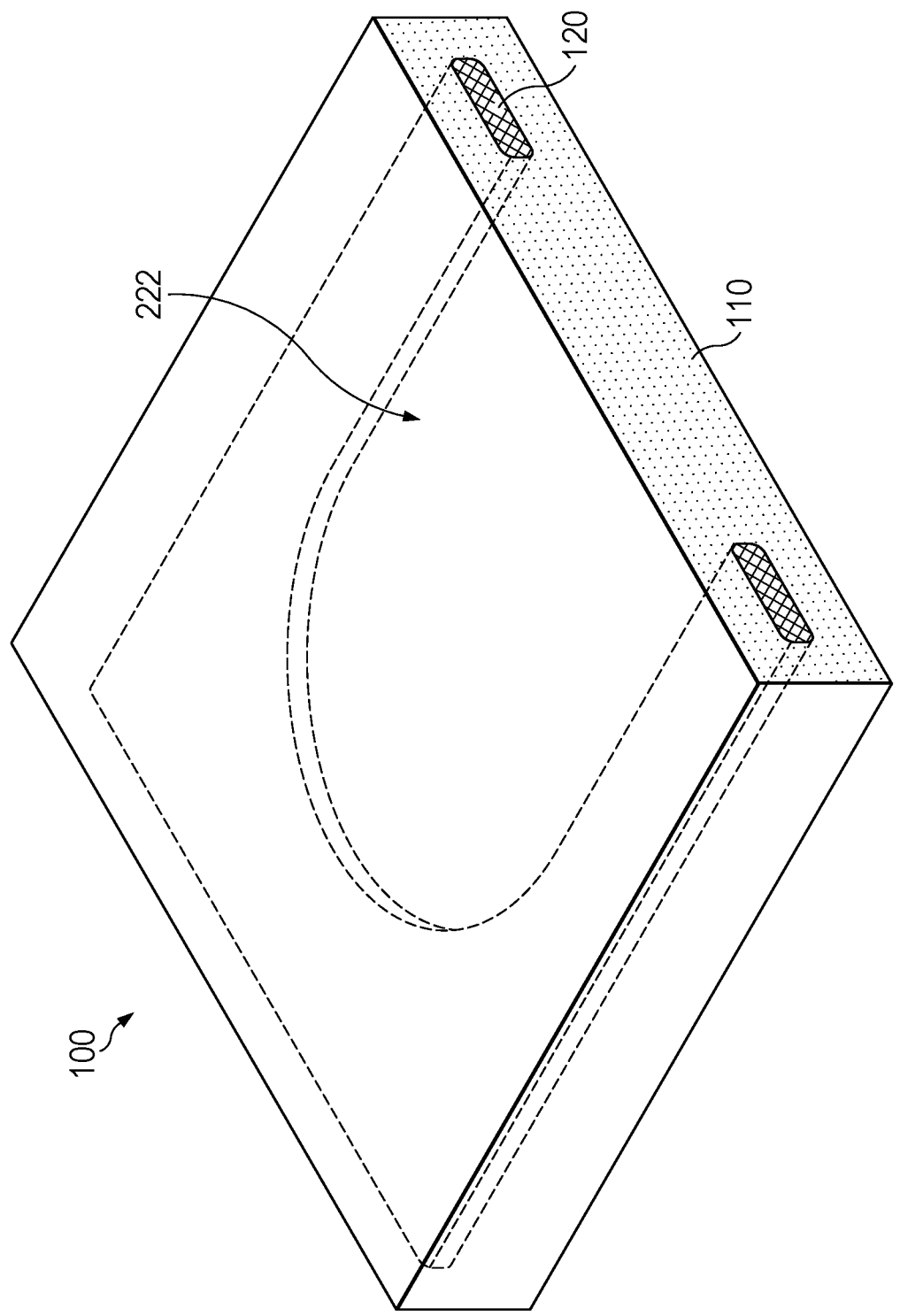
FIG. 2 is an illustrative representation of a cross-sectional, perspective view of an embodiment of a dressing of the present technology.
Figure 3:
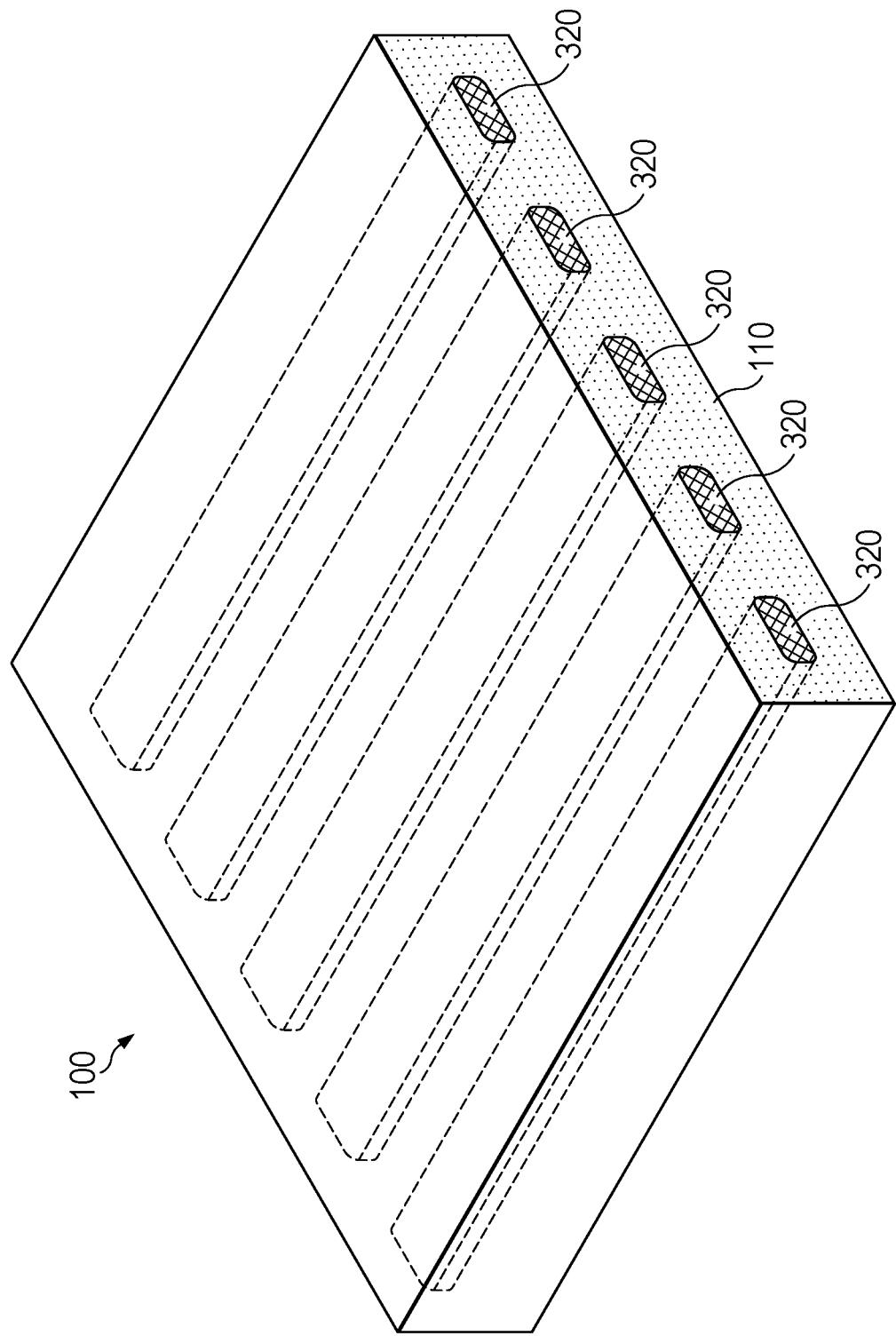
FIG. 3 is an illustrative representation of a cross-sectional, perspective view of an embodiment of a dressing of the present technology.

In any embodiment herein, the scaffold 120 may be embedded within or encapsulated by the contact layer. For example, as illustrated in FIG. 1, the scaffold 120 may be included as a sheet or layer embedded within the contact layer 110. While not illustrated in FIG. 1, the scaffold 120 embedded within the contact layer 110 may include one or more pores or apertures as discussed above. FIG. 2 illustrates another example, where the dressing 100 may include scaffold 120 as a sheet or layer having a border portion and defining an open central area 222. FIG. 3 illustrates yet another example, where the scaffold 120 includes a plurality of strips 320.

Figure 4:
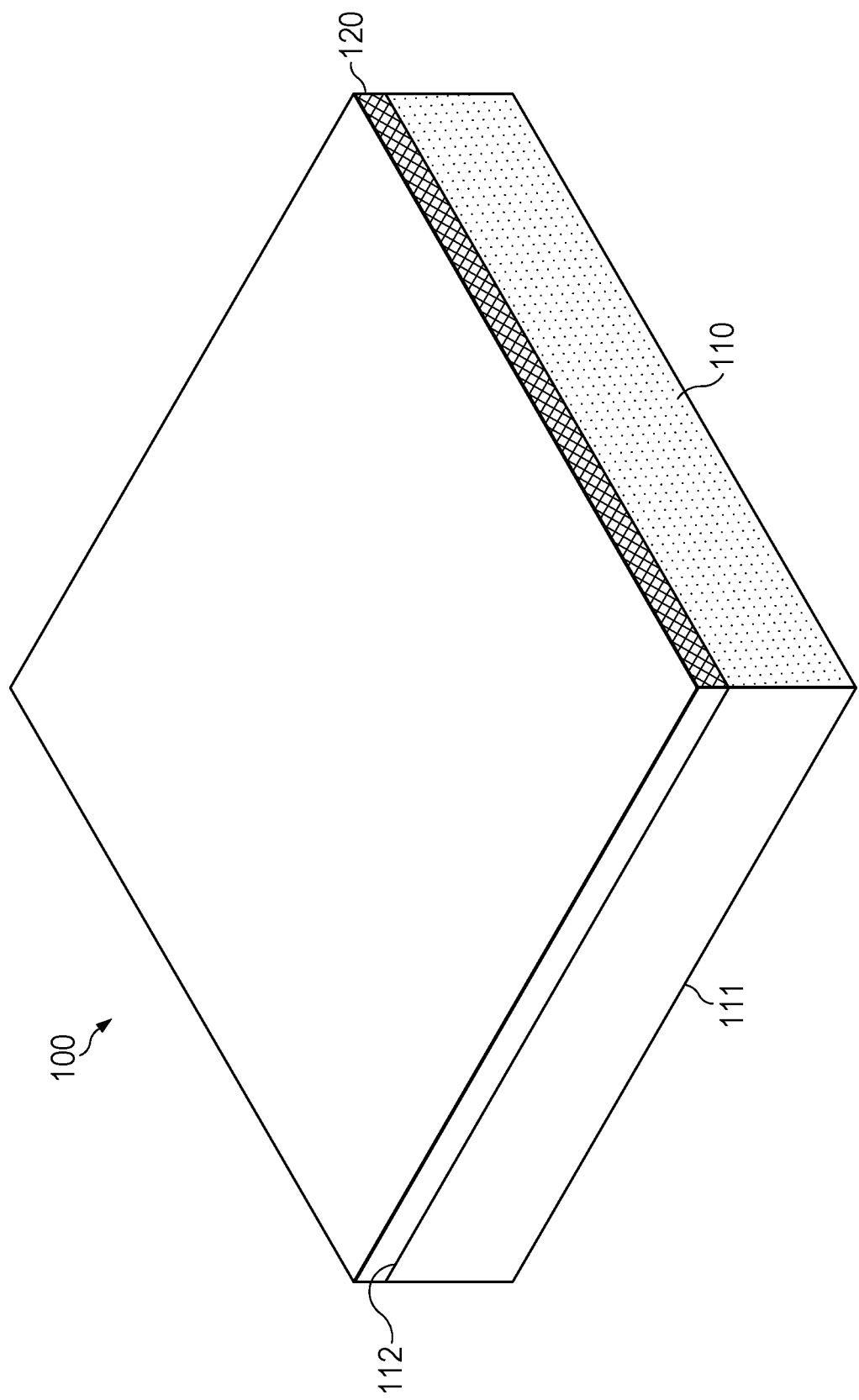
FIG. 4 is an illustrative representation of a cross-sectional, perspective view of an embodiment of a dressing of the present technology.
Figure 5:
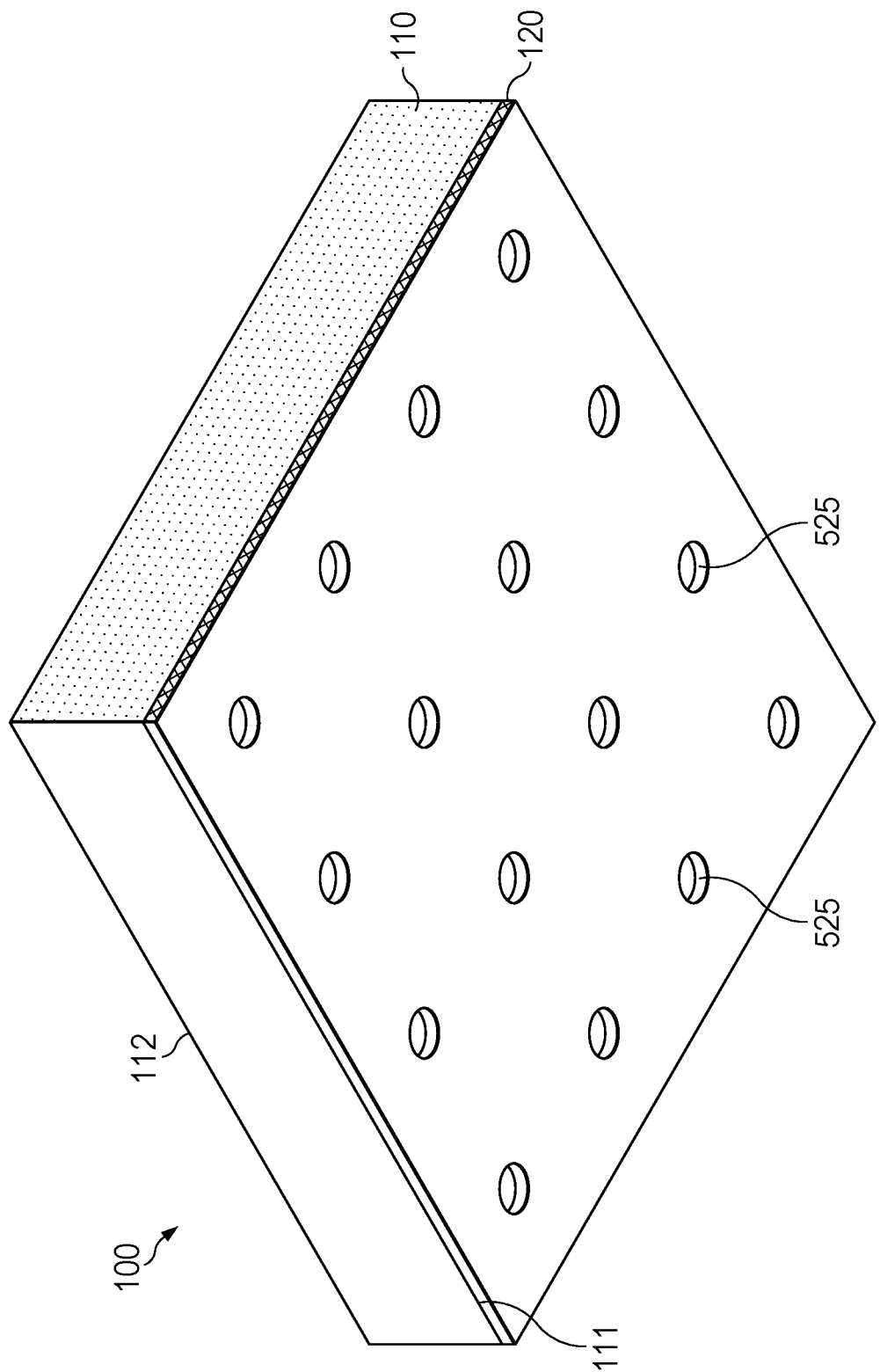
FIG. 5 is an illustrative representation of a cross-sectional, perspective view of an embodiment of a dressing of the present technology.

In any embodiment herein, the scaffold may be disposed adjacent to one or more surfaces of the contact layer, such as the first surface, the second surface, or both, and as further illustrated in the exemplary, non-limiting representations provided in FIGS. 4 and 5. In FIG. 4, the scaffold 120 is disposed adjacent to second surface 112 (e.g., a back surface) of contact layer 110. In FIG. 5, the scaffold 120 is in the form of a sheet or layer and includes a plurality of apertures 525, and where first surface 111 may be configured as a tissue-facing surface of contact layer 110.

Additional Layers

Figure 6:
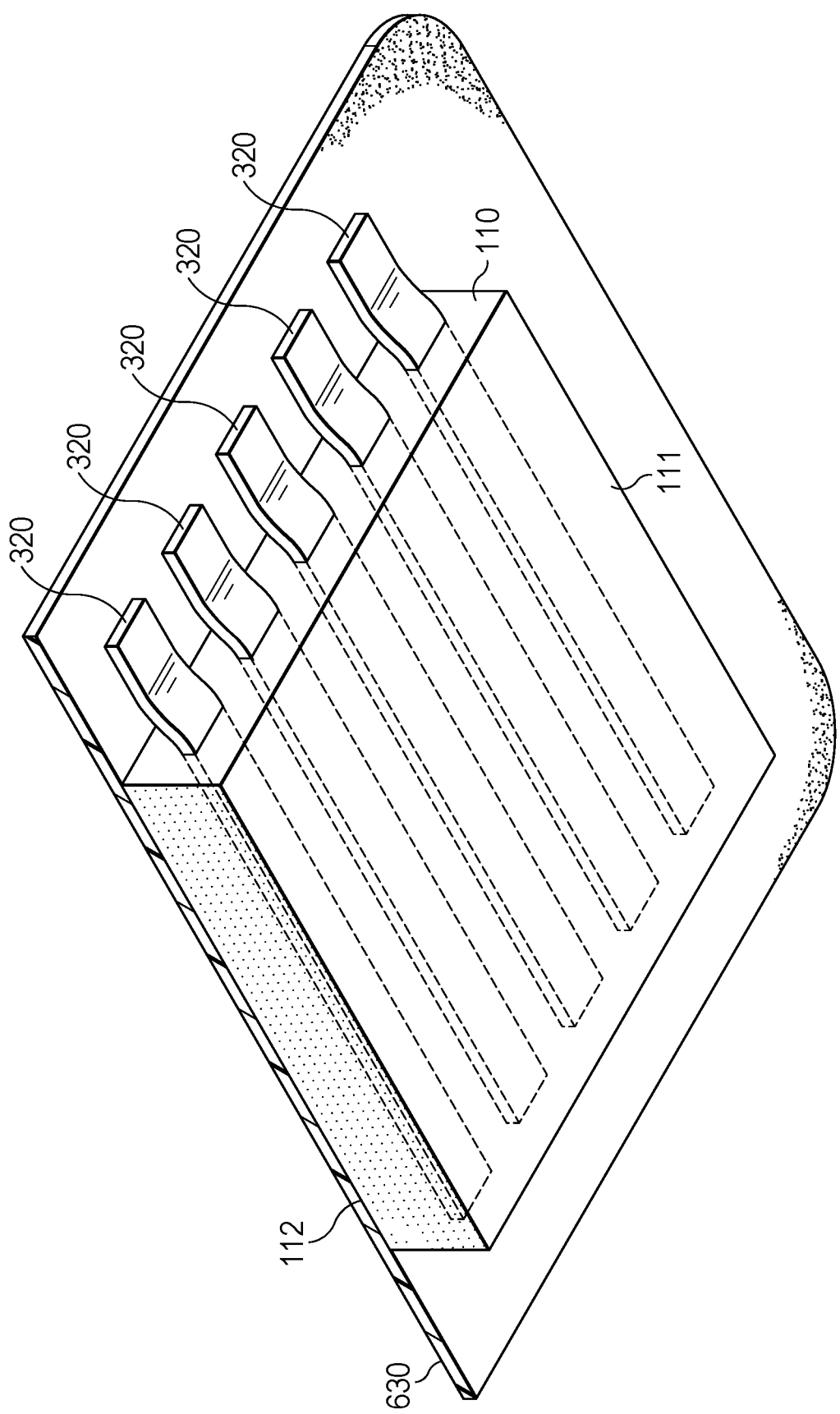
FIG. 6 is an illustrative representation of a cross-sectional, perspective view of an embodiment of a dressing of the present technology.

In any embodiment herein, the dressing may include one or more additional layers. The one or more additional layers may be configured to perform any of a variety of functions including, for example, adherence of the dressing to a tissue site or to surrounding tissues, increasing structural rigidity of the dressing, protection from moisture or other materials in the external environment, protection of a wound surface, delivery of one or more actives or other materials to the wound surface, or a combination of any two or more thereof. In any embodiment herein, the one or more additional layers may be conformable to a wound surface and/or to the surrounding tissues. For example, the one or more additional layers may be configured to be capable of bending such that the surfaces of the dressing facing a wound may be in substantial contact with the wound and/or the surrounding tissues. FIG. 6 is a non-limiting example of a dressing including one or more additional layers, where an additional layer is provided via cover 630 positioned over contact layer 110 adjacent to second surface 112.

In any embodiment herein, the one or more additional layers (e.g., cover 630 of FIG. 6) may generally be configured to provide a bacterial barrier and/or protection from physical trauma. In any embodiment herein, the one or more additional layers (e.g., cover 630 of FIG. 6) may be constructed from a material that can reduce evaporative losses and provide a fluid seal between two components or two environments, such as between a therapeutic environment and a local external environment—for example, an elastomeric film or membrane that can provide a seal at a tissue site for a given therapy—and may have a high moisture-vapor transmission rate (MVTR) (e.g., a MVTR of at least 300 g/m2 per twenty-four hours). In any embodiment herein, the one or more additional layers (e.g., cover 630 of FIG. 6) may be formed from a suitable polymer. For example, cover 630 of FIG. 6 may include a polymer drape, such as a polyurethane film, that may be permeable to water vapor but generally impermeable to liquid. The polymer drape may have a thickness in the range of about 25 microns to about 50 microns; thus, the polymer drape may have a thickness of about 25 microns, about 26 microns, about 27 microns, about 28 microns, about 29 microns, about 30 microns, about 31 microns, about 32 microns, about 33 microns, about 34 microns, about 35 microns, about 36 microns, about 37 microns, about 38 microns, about 39 microns, about 40 microns, about 41 microns, about 42 microns, about 43 microns, about 44 microns, about 45 microns, about 46 microns, about 47 microns, about 48 microns, about 49 microns, about 50 microns, or any range including and/or in between any two of the preceding values.

In any embodiment herein, the one or more additional layers (e.g., cover 630 of FIG. 6) may be configured to be attached to an attachment surface, such as undamaged epidermis, a gasket, or another cover, for example, via an attachment device. In any embodiment herein, the one or more additional layers (e.g., cover 630 of FIG. 6) may be attached to tissue proximate the tissue site, such as epidermis so as to form a sealed space. In such embodiments, the attachment device may take any suitable form, such as a medically-acceptable, pressure-sensitive adhesive that extends about a periphery, a portion, or an entire sealing member. For example, some or all of cover 630 of FIG. 6 may be coated with an adhesive, such as an acrylic adhesive, to provide a coating weight between about 25 to about 65 grams per square meter (g.s.m.). Thicker adhesives, or combinations of adhesives, may be applied, for example, to improve the seal and reduce leaks. Other examples of an attachment device may include a double-sided tape, a paste, a hydrocolloid, a hydrogel, a silicone gel, or an organogel.

Secondary Layer

Figure 8:
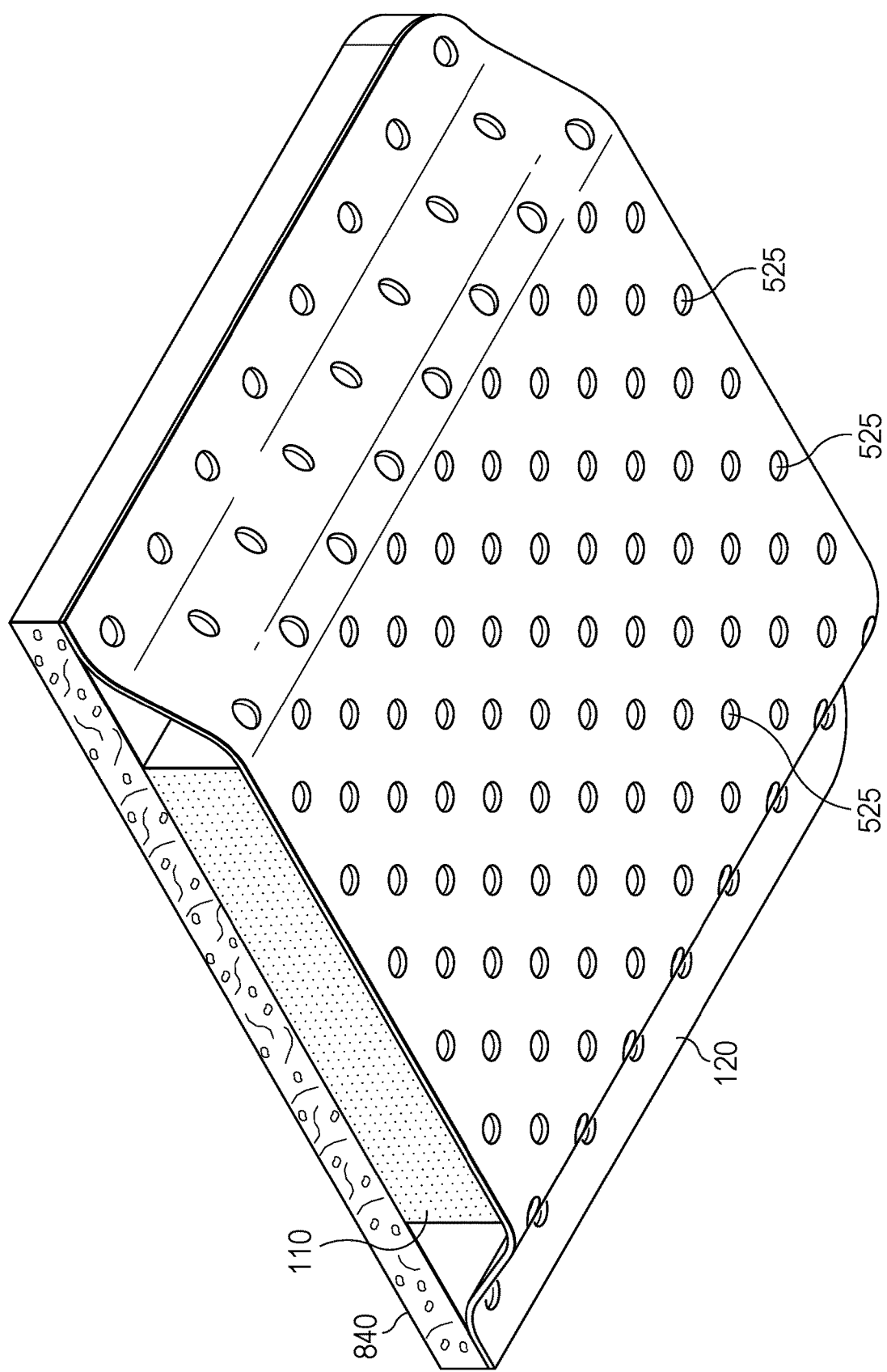
FIG. 8 is an illustrative representation of a cross-sectional, perspective view of an embodiment of a dressing of the present technology.

In any embodiment herein, the dressing may further include a secondary layer. The secondary layer may be positioned adjacent to the contact layer. FIG. 8 provides an example where secondary layer 840 is positioned adjacent to contact layer 110 and the dressing 100 includes scaffold 120 having a plurality of apertures 525. While not illustrated in FIG. 8, the secondary layer may include fluid pathways interconnected so as to improve distribution or collection of fluids. In any embodiment herein, the secondary layer may be a porous foam material having a plurality of interconnected cells or pores, for example, a cellular foam, an open-cell foam, a reticulated foam, a porous tissue collections, other porous materials such as gauze or felted mat generally including pores, edges, and/or walls adapted to form interconnected fluid pathways (e.g., channels), as well as a combination of any two or more thereof. In any embodiment herein, the secondary layer may include a porous foam (including pores) with an average pore diameter of about 400 microns to about 600 microns; thus, the porous foam may include an average pore diameter of about 400 microns, about 420 microns, about 440 microns, about 460 microns, about 480 microns, about 500 microns, about 520 microns, about 540 microns, about 560 microns, about 580 microns, about 600 microns, or any range including and/or in between any two of the preceding values. In any embodiment herein, the secondary layer may include an open-cell foam, such as reticulated polyurethane foam.

In any embodiment herein, the secondary layer may exhibit an absorbency of at least 3 g saline/g, (such as at least 5 g saline/g) and may exhibit an absorbency of about 8 to about 20 g saline/g. Thus, the secondary layer may exhibit an absorbency of about 3 g saline/g, about 4 g saline/g, about 5 g saline/g, about 6 g saline/g, about 7 g saline/g, about 8 g saline/g, about 9 g saline/g, about 10 g saline/g, about 11 g saline/g, about 12 g saline/g, about 13 g saline/g, about 14 g saline/g, about 15 g saline/g, about 16 g saline/g, about 17 g saline/g, about 18 g saline/g, about 19 g saline/g, about 20 g saline/g, or any range including and/or in between any two of the preceding values. In any embodiment herein, the secondary layer may be hydrophilic where the secondary layer may also absorb (e.g., wick) fluid away from the contact layer such as by capillary flow or other wicking mechanisms. An example of hydrophilic foam is a polyvinyl alcohol, open-cell foam as well as foams made from polyether. Other foams that may exhibit hydrophilic characteristics include hydrophobic foams that have been treated or coated to provide hydrophilicity.

Figure 7:
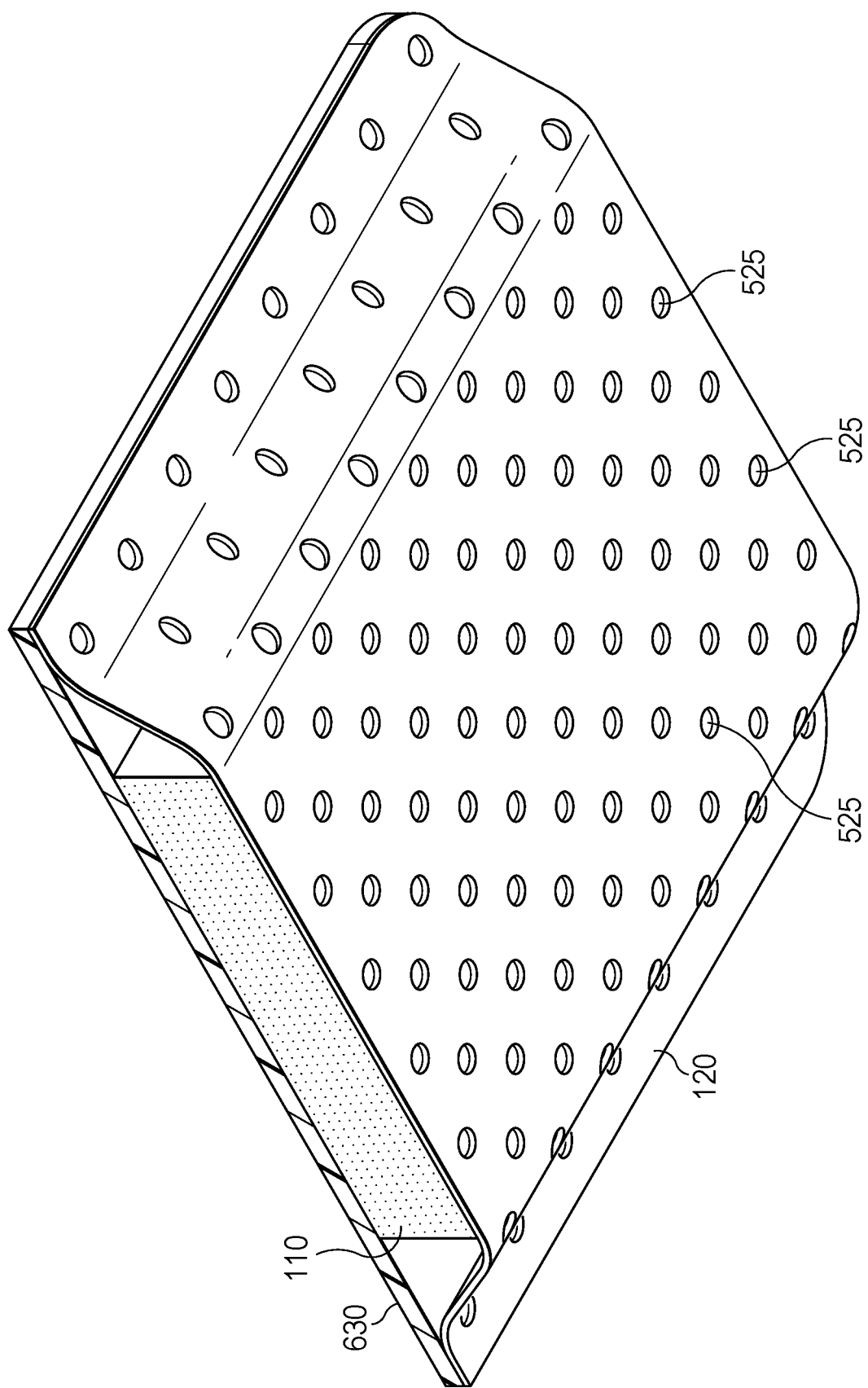
FIG. 7 is an illustrative representation of a cross-sectional, perspective view of an embodiment of a dressing of the present technology.

In any embodiment herein and as explained by reference to (but not being limited to) FIGS. 7 & 8, the scaffold (120) may be attached to the cover (630), the secondary layer (840), or both. For example, the scaffold (120) may be attached to the cover (630) and/or the secondary layer (840) to provide additional structural support to the contact layer (110). For example, the cover (630) and/or the secondary layer (840) may provide structural support to the contact layer (110) indirectly via the scaffold (120). FIG. 7 in particular illustrates dressing 100 that includes scaffold 120 having a plurality of apertures 525 and disposed adjacent to first surface 111 of contact layer 110. Scaffold 120 may be attached to cover 630 such that scaffold 120 and cover 630 cooperatively retain contact layer 110 in a desired conformation, for example, within a pocket substantially defined by scaffold 120 and cover 630. By way of another example and as explained by reference to (but not being limited to) FIG. 6, the cover (630) may impart structural support, via the scaffold (e.g., plurality of strips 320), to the contact layer in addition to structural support imparted to the contact layer (110) by the scaffold.

Therapy Methods

The present technology also provides a therapy method, where the therapy method includes positioning a dressing of any embodiment herein of the present technology with respect to the tissue site. For example, in operation, the dressing may be positioned proximate to a wound. For example, the contact layer and the scaffold may be placed within, over, on, or otherwise proximate to the tissue site. In embodiments where the dressing includes a cover, the cover may be placed over the contact layer and the scaffold and the cover sealed to an attachment surface near the tissue site. For example, the cover may be sealed to undamaged epidermis peripheral to a tissue site. In any embodiment herein the contact layer and scaffold may be positioned first and, after the contact layer scaffold have been positioned, the cover may be positioned. In any embodiment herein, the dressing may be preassembled, for example, such that the contact layer, the scaffold, and the cover are positioned with respect to each other prior to placement proximate the tissue site. For example, the various components of the dressing may be positioned with respect to the tissue site sequentially or, alternatively, may be positioned with respect to each other and then positioned with respect to the tissue site. Thus, the cover may provide a sealed therapeutic environment including the contact layer and the scaffold and proximate to a tissue site, substantially isolated from the external environment.

The dressing of any embodiment described herein may be employed in therapy where a tissue site is treated with reduced pressure. Treatment of tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits may increase development of granulation tissue and reduce healing times.

Figure 9:
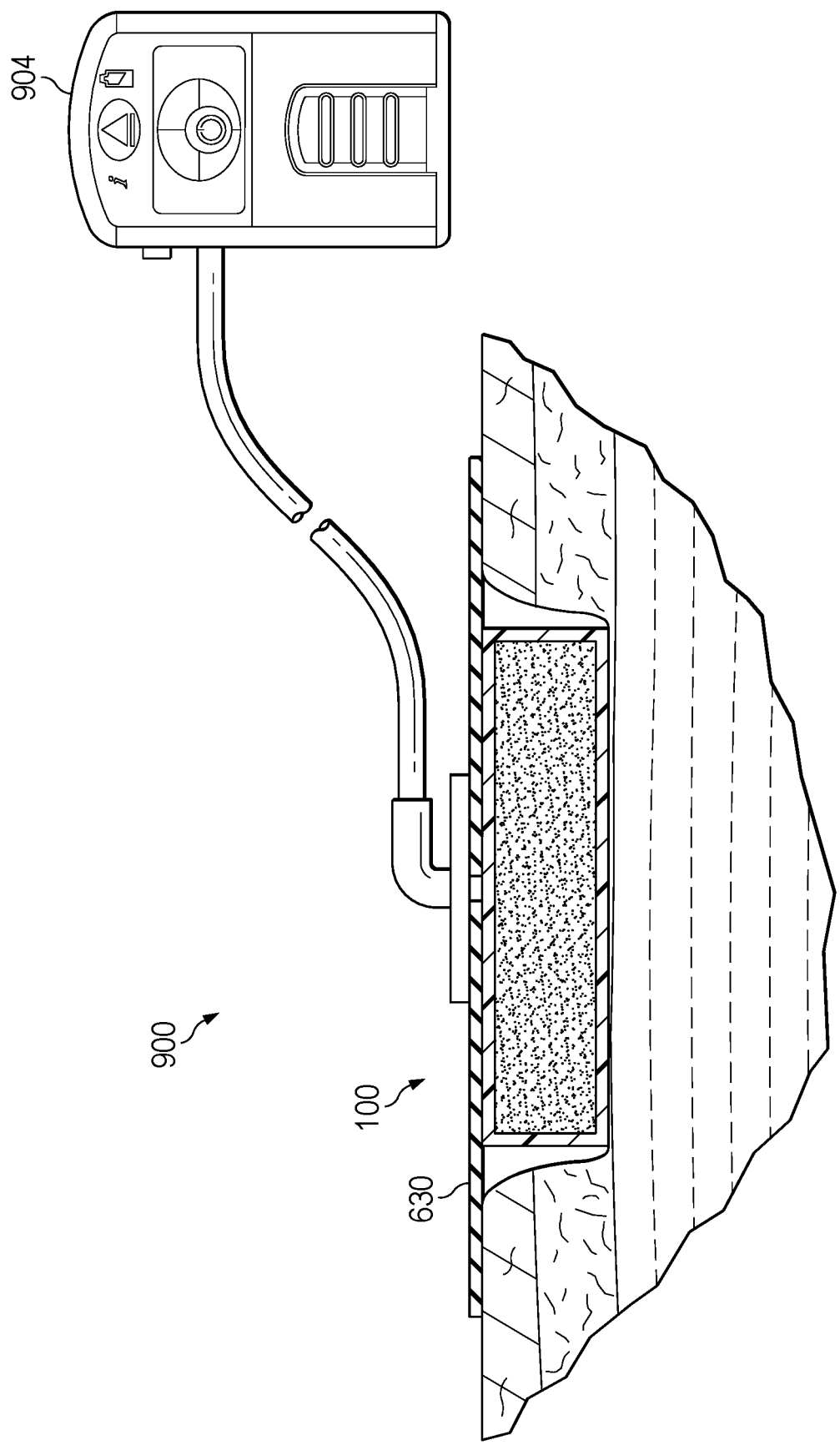
FIG. 9 is a simplified schematic diagram of an exemplary embodiment of a negative pressure therapy system including a dressing of the present technology.

For example, FIG. 9 illustrates a system (900) for negative-pressure therapy in a simplified schematic. Generally, the system may be configured to provide negative-pressure to a tissue site in accordance with this specification. In any embodiment herein, the system may generally include a negative-pressure supply, and may include (or be configured to be coupled to) a distribution component. In general, a distribution component may refer to any complementary or ancillary component configured to be fluidly coupled to a negative-pressure supply in a fluid path between a negative-pressure supply and a tissue site. In the illustration provided in FIG. 9, dressing 100 is an example of a distribution component fluidly coupled to negative-pressure source 904 such that negative pressure may be applied to a tissue site via dressing 100.

In any embodiment herein, the dressing may be configured to distribute negative pressure. The contact layer 110 and/or the scaffold 120 may include or be configured as a manifold. A "manifold" in this context generally includes any composition or structure providing a plurality of pathways configured to collect or distribute fluid across a tissue site under pressure. For example, a manifold may be configured to receive negative pressure from a negative-pressure source and to distribute negative pressure through multiple apertures (e.g., pores), which may have the effect of collecting fluid and drawing the fluid toward the negative-pressure source. More particularly, as illustrated by FIG. 9, the dressing (100) may be configured to receive negative pressure from a negative-pressure source (904) and to distribute the negative pressure to a tissue site, which may have the effect of collecting fluid from a sealed space provided by a cover (such as cover 630). For example, the negative-pressure source may draw fluid from a tissue site through the dressing. Additionally or alternatively, the fluid path(s) may be reversed or a secondary fluid path may be provided to facilitate movement of fluid across a tissue site. Additionally or alternatively the fluid pathways of a manifold may be interconnected to improve distribution or collection of fluids. Additionally or alternatively a manifold may be a porous foam material having a plurality of interconnected cells or pores. For example, open-cell foams such as reticulated foams generally include pores, edges, and/or walls that may form interconnected fluid pathways such as, channels.

The fluid mechanics associated with using a negative-pressure source to reduce pressure in another component or location, such as within a sealed therapeutic environment, can be mathematically complex. However, the basic principles of fluid mechanics applicable to negative-pressure therapy are generally well-known to those skilled in the art. The process of reducing pressure may be described generally and illustratively herein as "delivering," "distributing," or "generating" negative pressure, for example.

In general, a fluid, such as wound fluid (for example, wound exudates and other fluids), flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" may generally refer to a pressure less than a local ambient pressure, such as the ambient pressure in a local environment external to a sealed therapeutic environment provided by the dressing 100. In many cases, the local ambient pressure may also be the atmospheric pressure proximate to or about a tissue site. Alternatively, the pressure may be less than a hydrostatic pressure associated with the tissue at the tissue site. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa), gauge pressure. Common therapeutic ranges are between 50 mm Hg (−6.7 kPa) and −300 mm Hg (−39.9 kPa), gauge pressure.

Additionally or alternatively, in some embodiments, a negative-pressure supply (such as negative-pressure source 904 of FIG. 9), may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy. A negative-pressure source (e.g., negative-pressure source 904 of FIG. 9) may be combined with a controller and other components into a therapy unit. A negative-pressure supply may also have one or more supply ports configured to facilitate coupling and de-coupling of the negative-pressure supply to one or more distribution components.

In any embodiment herein, components may be fluidly coupled to each other to provide a path for transferring fluids (i.e., liquid and/or gas) between the components. For example, components may be fluidly coupled through a fluid conductor, such as a tube. As used herein, the term "fluid conductor" is intended to broadly include a tube, pipe, hose, conduit, or other structure with one or more lumina or open passages adapted to convey a fluid between two ends thereof. Typically, a fluid conductor may be an elongated, cylindrical structure with some flexibility, but the geometry and rigidity may vary. Additionally or alternatively, in some embodiments, the negative-pressure source may be operatively coupled to the dressing via a dressing interface. For example and by way of reference to FIG. 9, dressing 100 may be coupled to negative-pressure source 904 via a dressing interface such that dressing 100 receives negative pressure from negative-pressure source 904.

In any embodiment herein where the dressing includes a cover and the dressing is employed in the context of a negative-pressure therapy, the therapy method may include positioning the contact layer, the scaffold, and the cover proximate to a tissue site. The therapy method may further include sealing the cover to tissue surrounding the tissue site to form a sealed space. For example, the cover may be placed over the contact layer and/or scaffold and sealed to an attachment surface near the tissue site, for example, to undamaged epidermis peripheral to a tissue site.

The therapy method in any embodiment herein may further include fluidly coupling a negative-pressure source to the sealed space and operating the negative-pressure source to generate a negative pressure in the sealed space. For example, the negative-pressure source may be coupled to the dressing such that the negative-pressure source may be used to reduce the pressure in the sealed space. For example, negative pressure applied across the tissue site, for example, via the dressing may be effective to induce macrostrain and microstrain at the tissue site, as well as remove exudates and other fluids from the tissue site.

Advantages

The present technology provides provide significant advantages, including modulating enzyme activity.

Enzymes, such as proteases, may be destructive or detrimental to wound healing, particularly when an over-abundance of such proteases are present at a tissue site. Without wishing to be bound by theory, it is believed that, the contact layer of the present technology may advantageously modulate protease activity. For example, if the contact layer is used in a therapy, wound fluid may come into contact with the contact layer. Upon contact between the wound fluid and the contact layer, the contact layer may degrade and, as the contact layer degrades, can modulate protease activity. For example, and not intending to be bound by theory, ORC within a contact layer may be effective to modulate the activity of destructive enzymes such as elastase and matrix metalloproteinase (MMP) and neutrophil elastase. The contact layer and the dressing may modulate the activity of such enzymes, which may be beneficial to wound healing.

In any embodiment herein, it may be desirable to hydrate a contact layer (e.g., a collagen/ORC dressing, such as the PROMOGRAM™ Matrix Wound Dressing and the PROMOGRAN PRISMA™ Matrix, commercially available from Acelity, Inc. in San Antonio, Tex.) prior to application to a tissue site, for example, when the dressing is being applied to a dry wound or a wound with low exudate or wound fluid levels. The contact layer may be hydrated prior to application with a sterile saline solution, and the scaffolds of the dressings of the present technology may impart additional structural rigidity to the dressing, for example, to the contact layer such that the disclosed dressings better retain shape.

Additionally or alternatively, the dressing of the present technology may provide an improved tissue interface, for example, if employed in a negative-pressure therapy. For example, if used in a negative-pressure therapy, a contact layer such as the contact layer may be disposed between a wound bed and a secondary layer, such as an open-cell foam or other manifold. Upon the application of negative pressure, some portion of the contact layer may be drawn into the secondary layer and away from the wound bed. A scaffold such as the scaffold may be effective to reduce the amount of the contact layer drawn away from the wound bed and yield improved contact between the contact layer and the wound bed.

Equivalents

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

The invention claimed is:

1. A dressing comprising
a contact layer comprising a first surface configured to contact a tissue site in a subject, the contact layer comprising a bioresorbable material, the bioresorbable material comprising collagen and oxidized regenerated cellulose (ORC); and
a scaffold encapsulated by the contact layer and configured to structurally support the contact layer, the scaffold comprising a bioresorbable material.

2. The dressing of claim 1, wherein the contact layer exhibits protease-modulating activity under physiological conditions.

3. The dressing of claim 1, wherein the contact layer comprises a sponge.

4. The dressing of claim 1, wherein the scaffold comprises a woven substrate.

5. The dressing of claim 1, wherein the scaffold comprises a non-woven substrate.

6. The dressing of claim 1, wherein the scaffold comprises oxidized regenerated cellulose (ORC).

7. The dressing of claim 1, wherein the dressing further comprises a secondary layer positioned adjacent to the contact layer, wherein the secondary layer comprises an open-cell foam.

8. The dressing of claim 7, wherein the open-cell foam is hydrophobic.

9. The dressing of claim 7, wherein the open-cell foam comprises polyurethane.

10. The dressing of claim 1, wherein the contact layer further comprises a second surface, and the dressing further comprises a cover adjacent to the second surface.

11. A system for treating a tissue site with reduced pressure, the system comprising
a dressing of claim 1; and
a reduced-pressure source adapted to be fluidly coupled to the dressing.

12. A method for providing therapy to a tissue site, the method comprising positioning a dressing of claim 1 adjacent to the tissue site.

13. The method of claim 12, wherein
the contact layer further comprises a second surface, and the dressing further comprises a cover adjacent to the second surface; and
the method further comprises sealing the cover to the tissue surrounding the tissue site to form a sealed space.

14. The method of claim 13, the method further comprising
fluidly coupling a negative-pressure source to the sealed space; and
generating a negative pressure in the sealed space.

* * * * *